United States Patent [19]

Poncy

[11] Patent Number: 4,842,587
[45] Date of Patent: Jun. 27, 1989

[54] NO-PRICK HYPODERMIC SYRINGE

[76] Inventor: George W. Poncy, 3725 Investment La., Riviera Beach, Fla. 33404

[21] Appl. No.: 73,802

[22] Filed: Jul. 15, 1987

[51] Int. Cl.$^4$ .......................................... A61M 5/32
[52] U.S. Cl. ................................. 604/198; 604/263
[58] Field of Search ............... 604/198, 192, 263, 187

[56] References Cited

U.S. PATENT DOCUMENTS

| | | | |
|---|---|---|---|
| 2,571,653 | 10/1951 | Bastien . | |
| 2,623,520 | 12/1952 | Bamford et al. | 128/221 |
| 4,425,120 | 1/1984 | Sampson et al. | 604/198 |
| 4,631,057 | 12/1986 | Mitchell | 604/198 |
| 4,655,751 | 4/1987 | Harbaugh | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,772,272 | 9/1988 | McFarland | 604/198 |

FOREIGN PATENT DOCUMENTS 1200560 12/1959 France .
924734 5/1963 United Kingdom .

OTHER PUBLICATIONS

Advertisement in Hospital Purchasing News, Jan., 1987.
Article by Paul Berg in the Washington Post, Jun. 23, 1987, "Needle Designs Seek to Limit Disease Spread".

Primary Examiner—John D. Yasko
Attorney, Agent, or Firm—Lane and Aitken

[57] ABSTRACT

An assembly for preventing accidental pricking by a hypodermic syringe includes a cap mounted on a needle hub for sliding between an extended position enclosing the needle and a retracted position exposing the needle. The cap slides on resilient bands extending arcuately from flaps projecting radially from the needle hub and structure is provided to retain the cap in both its extended position and its retracted position. The cap is tapered toward an end distal to a body of the syringe so that the resilient bands snugly frictionally engage the distal end of the cap to maintain the cap in the retracted position. In one embodiment of the invention, the flaps include portions extending radially beyond the resilient band, and the cap defines channels for receiving the flaps. The channels widen abruptly, at their ends adjacent to the syringe, to define slots into which the radially extending portions of the flaps can be twisted to lock the cap in its extended position. In another embodiment, elongate axial ribs defined on the interior surface of the cap are received in gaps provided between the flaps and adjacent free ends of the arcuate resilient bands. In addition, annular beads are provided on the interior surface of the cap to retain the cap in its extended position and to prevent the separation of the cap from the needle hub.

25 Claims, 5 Drawing Sheets

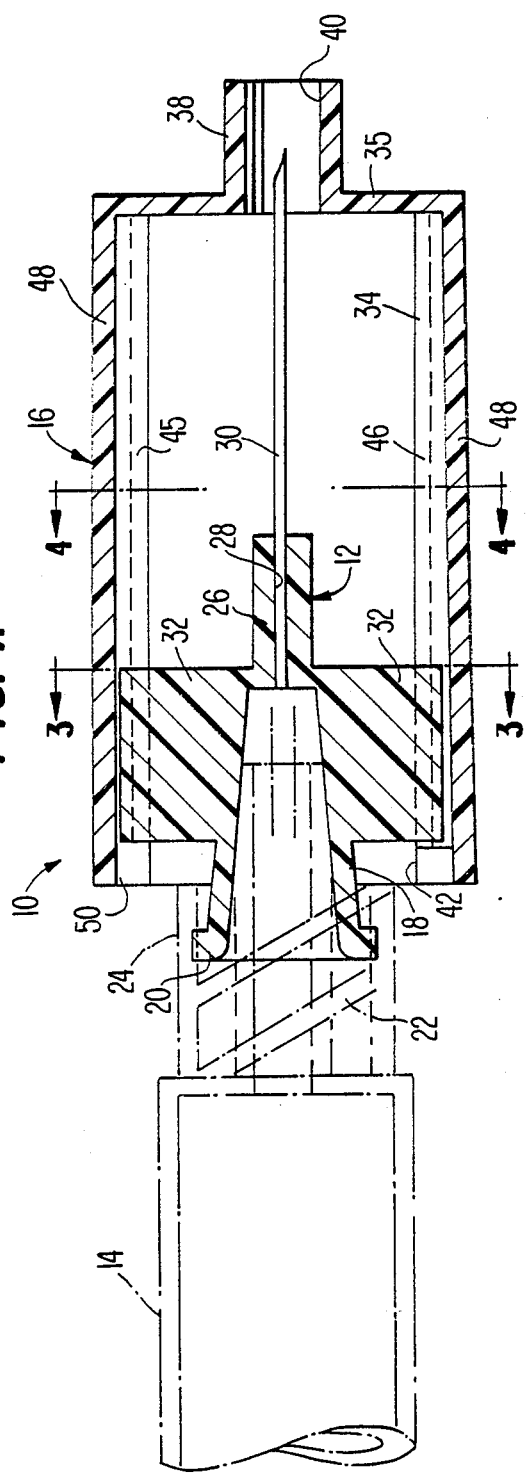
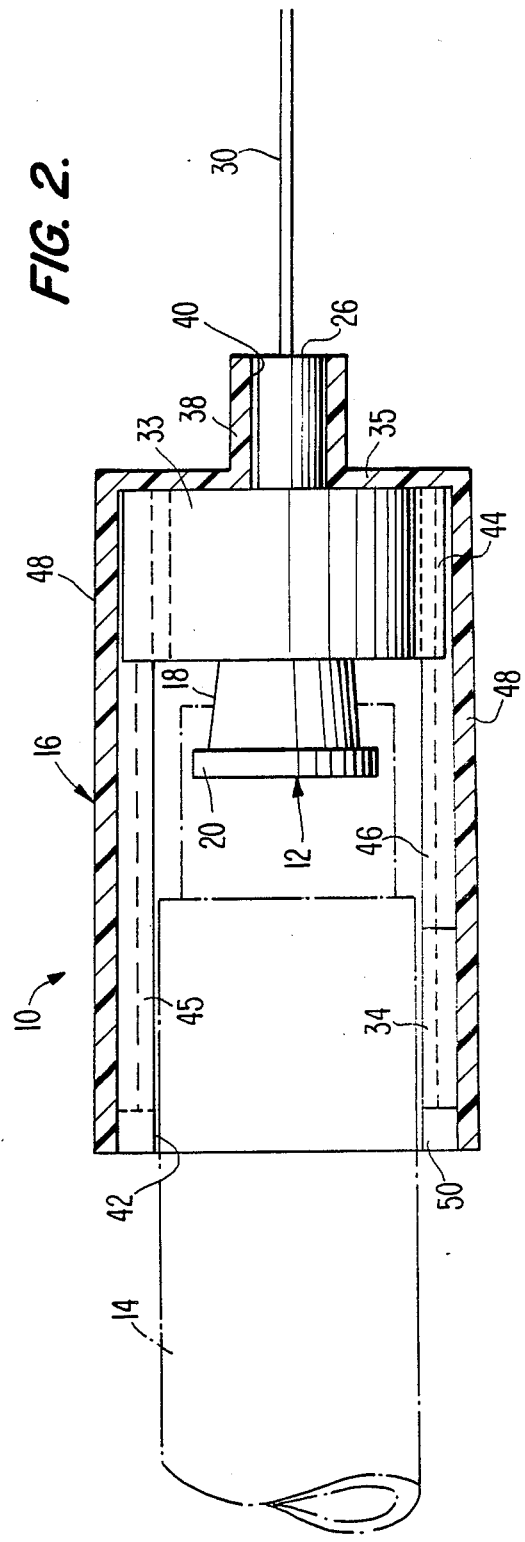

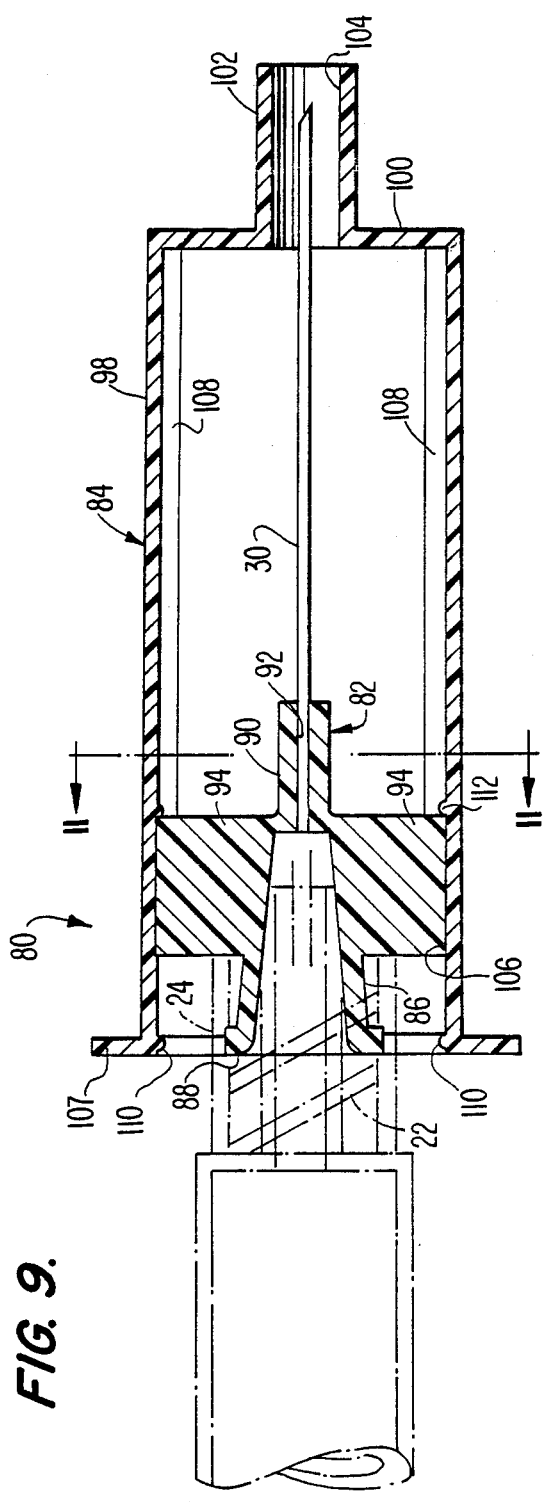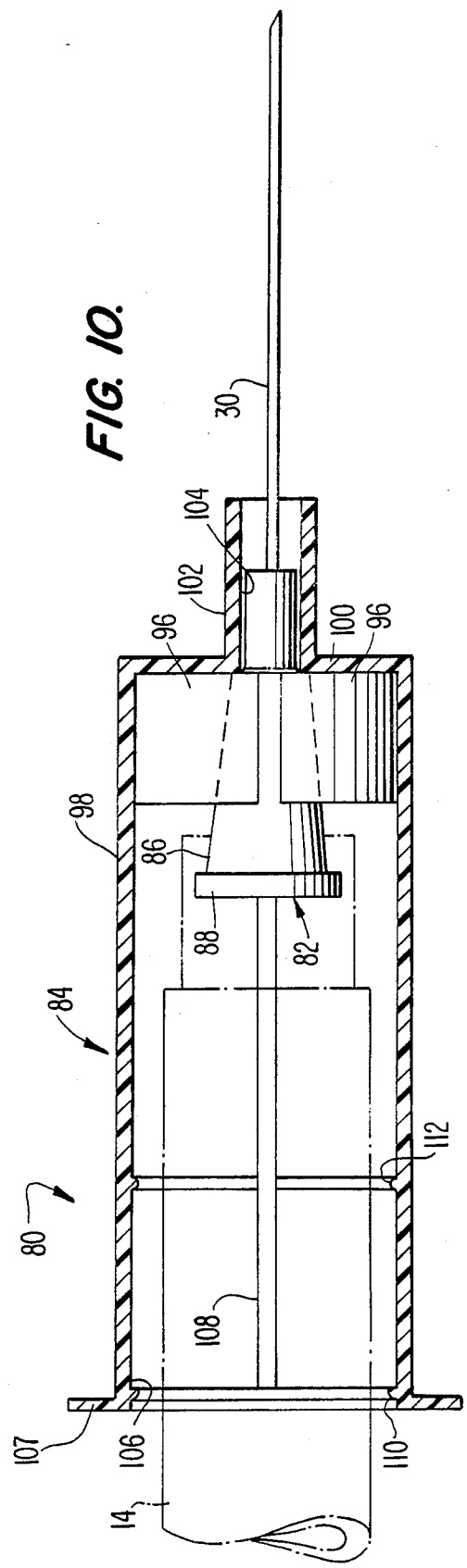

NO-PRICK HYPODERMIC SYRINGE

BACKGROUND OF THE INVENTION

This invention relates to hypodermic syringes for withdrawing blood or infusing a patient with serums and the like and, more particularly, to a hypodermic syringe designed to prevent accidental pricking of the fingers or hands of the person using the syringe.

Presently, the administration of an injection or blood withdrawal involves the removal of a protective cap covering the needle of a hypodermic syringe and, after the withdrawal of the needle from the body of a patient, the replacement of the cap over the needle before the entire hypodermic unit is discarded. Single-use hypodermic units are used in virtually all cases. The procedures just-described can easily lead to the accidental pricking of a hand or finger of the administrant, the injection of harmful viruses and bacteria under the skin, and the resultant infection of the administrant. In view of the increasing occurrence of fatal diseases such as Acquired Immune Deficiency Syndrome (AIDS), it is absolutely essential that accidental needle pricks be avoided.

Accidental pricking occurs most often during the removal and replacing of the needle cap. It is at these moments that the hand of the administrant is nearest to the sharp needle point. More specifically, the most common accidental pricking occurs because the cap is firmly held in place over the needle by friction between the cap and a hub in which the needle is mounted. A large frictional force is intentionally provided, such as by the engagement of ribs formed on an external surface of the needle hub and on an internal surface of the cap, so that the cap does not inadvertently become dislodged from the needle and, thereby, cause the previously sterile needle to become contaminated. In order to overcome the frictional resistance, the administrant must firmly grasp the cap and pull. The release of the cap from the needle hub occurs suddenly, so that there is a tendency for the hand to whip back towards the exposed needle, causing an accidental prick to occur. Accidental pricking also occurs when the cap is being replaced over the needle, since the opening in the cap into which the needle must be inserted is quite small. As a result, a slight misjudgment or unsteadiness causes the needle, instead of entering the small cap opening, to miss the opening and prick the finger of the administrant, which, by virtue of holding the cap, must of necessity be near the cap opening. In fact, such accidental pricking occurs even though caps of excessive length are used to cover even a short needle in an effort to increase the distance between the needle and the administrant's hand. For example, a cap used to cover a 1½ inch long needle may be as much as 2 inches long.

SUMMARY OF THE PRESENT INVENTION

The problems of accidental pricking in the removal and replacement of caps on hypodermic units is overcome in the present invention by incorporating a closure in the form of a cap as an integral part of the hypodermic unit, so that the cap requires no removal or replacement. The cap is slidably mounted on formations projecting from a hub in which the needle is mounted. The projecting formations include flaps projecting radially from the hub and resilient bands extending arcuately from the flaps to contact and guide the cap, maintaining the longitudinal axis of the cap in substantial alignment with the longitudinal axis of a syringe needle. As a result, any danger of the needle piercing a sidewall of the cap, especially during the sliding of the cap, is avoided. The hub has a bollow base end defining a flange which is connected to a hub of the syringe by, for example, engagement with internal spiral male threads, thereby defining a Luer lock, which is known in the art. The cap has a diameter larger than the diameter of the syringe and a proximal end which is open to permit the cap to move down over the syringe and slide on the arcuate resilient bands. An opposite end of the cap is closed in the sense that there is no opening large enough for a finger to enter and come into contact witb the needle. There is, however, an opening large enough for the needle to pass through to reach an exposed position in which an injection or withdrawal can be administered.

The cap is generally cylindrical but tapers slightly from the proximal end toward the opposite end in order to retain the cap in a retracted position in which the needle is exposed. The retention is accomplished by a snug frictional fit of the arcuate resilient bands in the tapered opposite end of the cap. In addition, structure is provided for retaining the cap in an extended position enclosing the needle, and further structure is included for preventing the cap from separating from the needle and the needle hub. Moreover, a mechanism is provided to permit the needle hub to be screwed onto a syringe body, for example, in a Luer lock, by rotating the cap relative to the syringe body.

In one embodiment of the invention, the flaps extend radially beyond the arcuate resilient bands, and the cap defines elongate axial channels which receive the radially extending portions of the flaps so that the cap can slide between the extended position enclosing the needle and the retracted position exposing the needle. The channels include abruptly wider portions near the end of the cap proximal to the syringe to define slots into which the flaps can be moved upon twisting of the cap relative to the syringe. A resilient detent member defined on a flange at the proximal end of the cap retains the flaps in the slots, and shoulders at the distal ends of the slots retain the cap in its extended position enclosing the needle. Rotation of the cap results in boundaries of the channels contacting the flaps to rotate the flaps and permit the needle hub to be screwed onto a syringe barrel. Various arrangements are provided to keep the cap from separating from the needle hub.

In another embodiment of the invention, the cap is retained in the extended position by the engagement of the resilient bands with an annular interference bead on the inner surface of the cap, spaced from the proximal end of the cap, and the separation of the cap from the needle and the needle hub is prevented by the engagement of the resilient bands with an annular stop bead on the inner surface of the cap adjacent the proximal end. Iln addition, elongate axial ribs on the interior surface of the cap are received in gaps provided between the flaps and adjacent free ends of the arcuate resilient bands. Rotation of the cap causes the elongate ribs to push the bands and, thereby, rotate the needle hub to screw it onto the barrel of the syringe.

BRIEF DESCRIPTION OF THE DRAWINGS

FIG. 1 is a cross section of one embodiment of the no-prick syringe assembly according to the present invention, in which the cap is in an extended position enclosing the needle;

FIG. 2 is a cross section of the syringe assembly FIG. 1, in which the cap is in a retracted position exposing the needle, and a needle portion is shown in side elevation;

FIG. 9 is a cross section of another embodiment of the no-prick syringe assembly according to the present invention, in which the cap is in an extended position enclosing the needle;

FIG. 10 is a cross section of the syringe assembly of FIG. 9 in which the assembly is rotated 90 degrees relative to FIG. 9, the cap is in a retracted position exposing the needle, and a needle portion is shown in side elevation;

DETAILED DESCRIPTION OF THE PREFERRED EMBODIMENT

Figure 3:
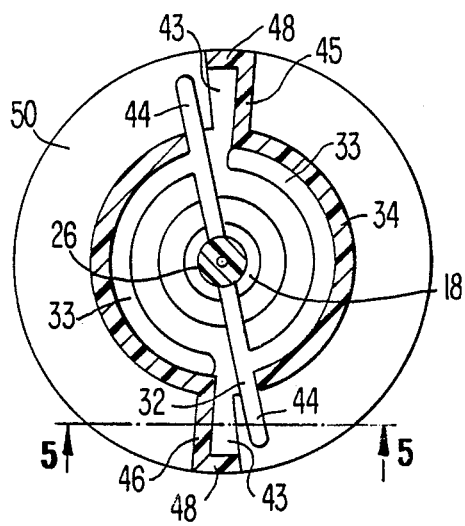
FIG. 3 is a cross section taken along the line 3—3 of FIG. 1.

As can best be seen from FIGS. 1 and 2, the non-pricking syringe assembly, which is designated generally by the reference numeral 10, includes a needle portion 12 mounted on a syringe body 14 and an elongate closure or cap portion 16 enclosing the needle portion 12. Both the needle portion 12 and the cap portion 16 are made of a plastic material, and preferably of a very rigid plastic having only very slight compressibility, such as a polycarbonate plastic, for example, the plastic sold under the tradename LEXAN. Such a plastic is very strong in thin sections and has glass-like clarity. The needle portion 12 has a hollow conical needle hub 18 With a rim 20 at its base for cooperating with internal spiral male threads 22 on a hub 24 of the syringe body 14 for mounting the needle hub 18 to the syringe body 14 in a conventional Luer lock. The assembly of the needle portion 12 and the cap portion 16 can be done by the manufacturer, and the resulting unit can be packaged to be attached to a syringe of choice at the point of use. As an alternative, the needle hub 18 can be molded to the hub 24 of the syringe body 14 to form an airtight frictional connection. A cylindrical post 26 defined at an end of the needle hub 18 opposite the base has a bore 28 for receiving a needle 30. A plurality of flaps 32 project radially from the needle hub 18, and an arcuate resilient band 33 having a radius equal to the radius of the internal surface of a generally cylindrical cap body 34 extends from each flap 32 to a free end spaced by a gap from an adjacent flap 32. A gap of 20 degrees, for example, between the free end and the adjacent flap 32 has been found to be suitable. Although the material for the flaps 32 and the bands 33 can be a very rigid plastic, such as LEXAN, such a plastic has sufficient resiliency to bias the bands 33 into snug contact with the internal surface of the cap body 34 and thereby maintain the longitudinal axis of the cap body 34 in substantial alignment with the longitudinal axis of the needle 30, whereby the cap portion 16 reciprocates smoothly on the bands 33 without substantial wobbling. The bands 33 are integral with flaps 32, and the area of their interaction acts as a resilient hinge urging the bands 33 against the surface of the cap body 34. Both the cap body 34 and the bands 33 are slightly tapered from their ends which are proximal to the syringe body 14 to their ends which are distal to the syringe body. A taper of 2 degrees, for example, has been found to be suitable, although the taper is exaggerated in the drawings for clarity of illustration. Due to the slight taper of the cap body 34, the bands 33 engage the interior surface of the cap body 34 even more snugly when the bands 33 are positioned at the distal end of the cap body. In this way, the cap portion 16 is retained in a retracted position exposing the needle 30 and facilitating the administration of an injection to or withdrawal from a patient. The generally cylindrical cap body 34 has a shoulder 35 and a hollow cylindrical cap extension 38 defining an opening 40 of a reduced diameter large enough to allow tbe needle 30 to pass through, but small enough to prevent a human finger from passing through. A small cap (not shown) can be provided to cover the extension 35 in a friction fit to prevent any accidental contamination of the needle 30 prior to use. The end of the cap body 34 proximal to tbe syringe body 14 defines an opening 42 large enough to permit the cap body 34 to fit over the syringe body 14.

Figure 4:
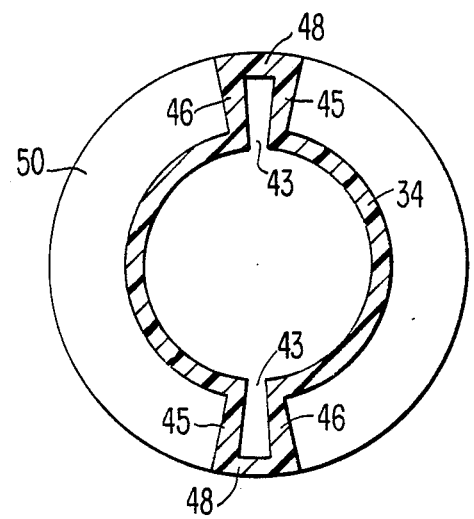
FIG. 4 is a cross section of the cap taken along the line 4—4 of FIG. 1.
Figure 5:
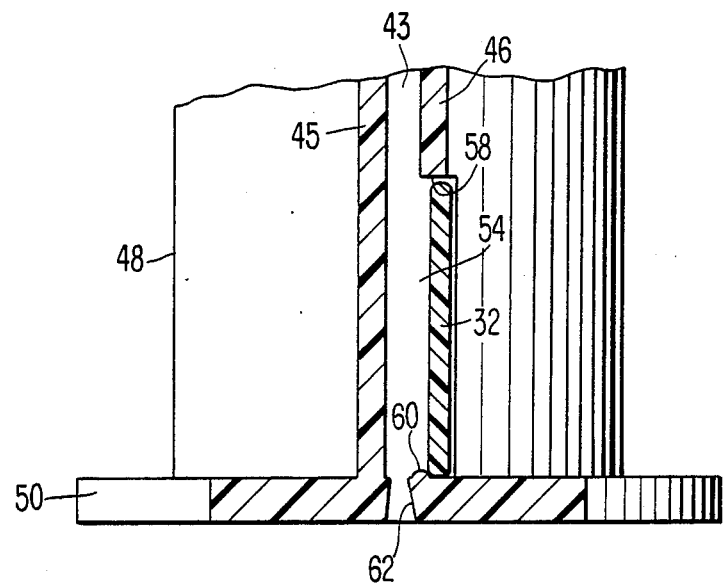
FIG. 5 is a view taken along the line 5—5, with parts in section, of the syringe assembly of FIG. 3.

As can be seen from FIGS. 3 and 4, when viewed in connection with FIGS. 1 and 2, the cap body 34 includes a plurality of elongate axial channels 43, the number and spacing of which corresponds to the number and spacing of the flaps 32 projecting from the needle hub 18. The flaps 32 include portions 44 which extend radially beyond the connections with the arcuate resilient bands 33. The radially extending portions 44 project into the channels 43 and are slidable in the channels. Although two flaps 32 and associated channels 43 are shown, it is understood that other numbers of flaps 32 and a corresponding number of channels 43 can be used. A corresponding number of arcuate resilient bands 33 would also be used. Ribs 45 and 46 extend radially from the cap body 34 and are connected at their radially outer ends by a wall 48 to define the sides and bottom of each channel 43. The outer surface of each wall 48 is flush with the outer circumference of a flange 50 defined at the proximal end of the cap body 34, wherein the flange defines the proximal end of the channel 43. As can best be seen from FIG. 5, each channel 43 widens abruptly at the proximal end of the cap body 34 to define a blind slot 54, the slot 54 being approximately equal in length to the length of the radially extending portions 44 of the flaps 32. Each slot 54 is defined in part by a shoulder 58 located at the distal end of the slot 54 adjacent to the center of the cap body 34.

As can be seen from FIGS. 1, 2, 3 and 5, the needle portion 12 fits within the cap portion 16 so that the radially extending portions 44 of the flaps 32 ride in the elongate channels 43. When the cap portion 16 is in its extended, needle-enclosing position, it can be twisted relative to the needle portion 12 so that the slots 54 move from a first orientation, in which the radially extending portions 44 of the flaps 32 are in alignment with long portions of the channels 43 and are external to the blind slots 54, to a second orientation, in which the radially extending portions 44 are in the blind slots 54. Since the blind slots 54 lie on the counterclockwise side of the channels 43, as viewed in FIG. 3, the twisting of the cap portion 16 to move the radially extending portions 44 into the slots 54 tends to further tighten the Luer lock between the needle hub 18 and the syringe hub 24. Similarly, where the non-pricking syringe assembly is to be attached to a syringe at the point of use, the rim 20 of the needle hub 18 can be screwed into engagement with the internal male threads 22 of the syringe hub 24 by rotating the cap portion 16, since such rotation causes a portion of the material of the cap portion 16 defining the slots 54 to contact the radially projecting portions 44 of the flaps 32 and rotate the needle portion 12 with the cap portion 16.

A shallow resilient rib 60 projecting into each blind slot 54 from the flange 50 acts as a detent for locking the flaps 32 in the blind slot 54 to prevent accidental pivoting of the flaps 32 out of the blind slot, which would permit the flaps to move forward in the channels 43, and thereby, permit the needle 30 to project beyond the cap portion 16. When the flaps 32 are in the blind slots 54, they are prevented, by engagement with the shoulders 58, from moving toward the distal end of the cap body 34 and exposing the needle 30. In order for the flaps 32 to be moved into the blind slots 54, the resistive force of the resilient ribs 6 must be overcome, since the distance between the resilient ribs 60 and the shoulders 58 is slightly less than the axial length of the flaps 32. When the flaps 32 are in the channels 43 but out of the blind slots 54, the cap portion 16 can be moved toward the syringe body 14 so that the needle 30 projects forward.

Figure 6:
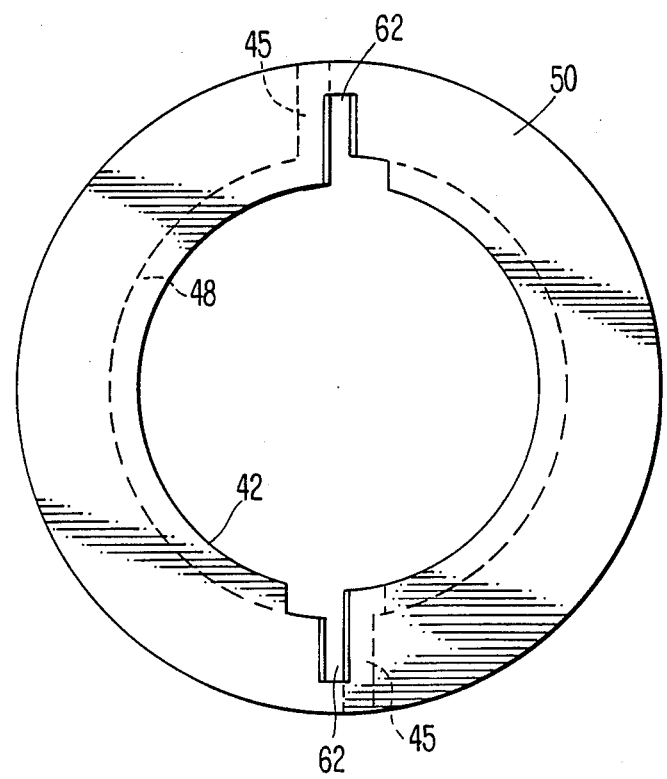
FIG. 6 is a bottom view of the cap of FIG. 5.

In order that the cap portion 16 can be placed over the needle portion 12 when the syringe assembly 10 is being assembled, slots 62 are defined in the flange 50 to permit the flange to move past the radially extending portions of the flaps 32. In one embodiment of the invention, as can best be seen from FIGS. 5 and 6, the slots 62 taper toward the distal end of the cap body 34 to a width less than the thickness of the flaps 32. The materials of flange 50 and the radially extending portion 44 of the flaps 32 are sufficiently resilient that the radially extending portions 44 can be forced through the slots 62 and into the cap body 34. Due to their tapered shape, the slots 62 prevent the flaps 32 from moving back outside the cap body 32. Thus, a mechanism is provided for assuring that the cap portion 16 does not separate from the needle portion 12 due to, for example, the momentum of pushing the cap portion forward from its needle-exposing position to its needle-enclosing position.

The hypodermic syringe assembly 10 according to the present invention is intended to come from the manufacturer with the flaps 32 held in the blind slots 54 to lock the cap portion 16 in its extended position enclosing the needle 30. The administrant of an injection or fluid withdrawal holds the syringe body 14 in one hand and, with the other hand, twists the cap portion so that the flaps 32 overcome the resiliency of the shallow ribs 60 to move out of the blind slots 54 and into alignment with the long portions of the elongate channels 43. The administrant pulls the cap portion 16 back until the needle 30 is fully exposed, in which position the cap portion 16 is retained by the snug frictional engagement between the arcuate resilient bands 33 and the tapered distal end of the cap body 34. The injection or withdrawal is administered, and the cap portion 16 is pushed forward and twisted again to lock the cap portion 16 in its extended, needle-enclosing position.

Figure 7:
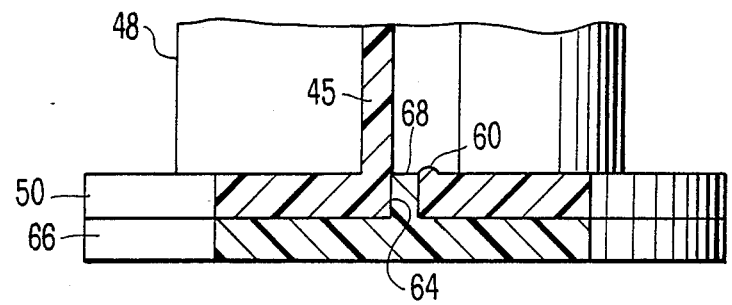
FIG. 7 is a partial view, similar to FIG. 5, showing an alternate arrangement for preventing the cap from separating from the needle hub.

In another embodiment of the invention, which is illustrated in FIG. 7, slots 64 through the flange 50 are not tapered, but a retainer ring 66 is secured to the flange 50 after the flaps 32 are moved through the slots 64 into the channels 43 in order to insure that the flaps 32 are retained within the cap body 34. The retainer ring 66 has inner and outer diameters corresponding to the inner and outer diameters of the flange 50 and ribs 68 for filling the slots 64 in a press fit. Thus, the retainer ring 66 can be put into position last and can fit over the syringe body 14 for placement against the flange 50, so that the ribs 68 are retained in the slots 64.

Figure 8:
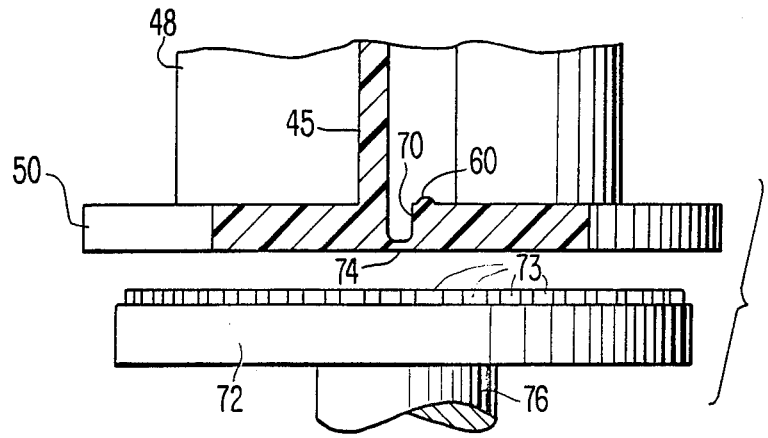
FIG. 8 is a partial view, similar to FIG. 5, of still another arrangement for preventing the cap from separating from the needle hub.

As another alternative to the tapered slots 62, as is best shown in the flange 50 of FIG. 8, slots 70 in the flange 50 are formed with parallel sides to permit the flaps 32 to pass through without interference upon assembly. However, when the flaps 32 are within the cap body 34, a heating die 72 having an annular shape corresponding generally to the shape of the flange 50 and teeth 73 projecting toward the flange 50 is brought into contact with the flange 50. The heat of the die 72 softens the material of the flange 50, and the die 72 is rotated slightly relative to the flange 50 so that the softened material obliterates the slots 70. The die 72 is withdrawn and the material of the flange 50 is allowed to cool, whereupon bridges 74 of material integral with the flange 50 block the slots 70 and retain the flaps 32 in the cap body 34. The die 72 can include an electrical resistance heating element connected to a thermostat (neither of which is shown) and a rotary shaft 76.

Figure 11:
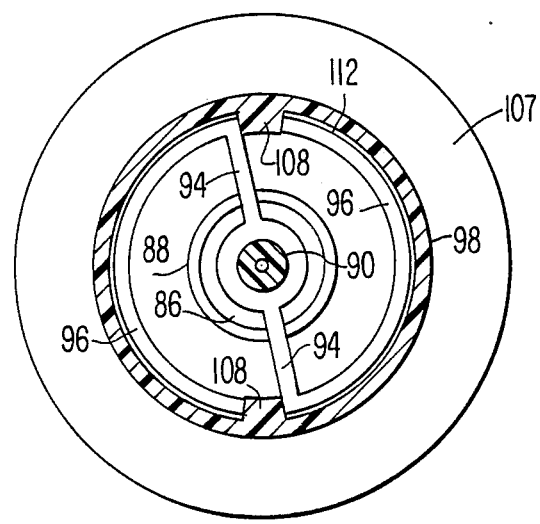
FIG. 11 is a cross section taken along the line 11—11 in FIG. 9.

In another embodiment of the no-prick syringe assembly according to the present invention, which can be seen in FIGS. 9–11 and in which the assembly is designated generally by the reference numeral 80, the structure and operation of the assembly is generally like that of the assembly 10, shown in FIGS. 1–8 and just described, but differs as to certain features. A needle portion 82 is mounted on a syringe body 14, and a closure or cap portion 84 encloses the needle portion 82. The needle portion 82 includes a hollow conical needle hub 86 with a rim 88 for connecting with the male threads 22 of the syringe body 14 in a Luer lock. A cylindrical post 90 on the needle hub 86 has a bore 92 for receiving the needle 30. A plurality of flaps 94 project radially from the needle hub 86, and an arcuate resilient band 96 extends from the radially outer end of each flap 94 to a free end spaced by a gap from an adjacent flap 94. A gap of 16 degrees, for example, has been found to be appropriate. The bands 96 are integral with the flaps 94 and have a radius substantially equal to the radius of the internal surface of a generally cylindrical cap body 98. The areas of intersection of the bands 96 and the flaps 94 act as spring-loaded hinges to bias the bands 96 against the cap body 98, whereby the cap body can reciprocate on the bands without substantial wobble, thereby maintaining the longitudinal axis of the cap body 98 substantially aligned with the longitudinal axis of the needle 30. The cap body 98 is slightly tapered, for example, a taper of 2 degrees, from its end proximal to the syringe body 14 to its end distal from the syringe body, and the arcuate resilient bands 96 may be tapered in the same sense. In this way, the cap portion 84 is retained in a retracted position exposing the needle 30. The cap body 98 has a shoulder 100, a hollow cylindrical cap extension 102, a reduced-diameter opening 104, and a large opening 106, all of which are similar to corresponding parts in the first embodiment. In addition, the cap body 98 includes an exterior annular flange 107 at its proximal end.

As can be seen from FIG. 11, when viewed together with FIGS. 9 and 10, elongate axial anti-twist ribs 108 are defined on the interior of the cap body 98 in a number corresponding to the number of arcuate resilient bands 96. The ribs 108 project into the gaps between the free ends of the bands 96 and their adjacent flaps 94, thereby permitting reciprocation of the cap body 98 relative to the needle portion 82 while preventing rotation of the cap body relative to the needle portion. Therefore, the needle portion 82 can be screwed onto the syringe body 14 by rotating the cap body 98. In addition, the width of the ribs 108 is made slightly larger than the width of the gaps, for example, 16.5 degrees compared to 16 degrees, to force the free ends of the bands 96 away from the adjacent flaps 94 and against the cap body 98 in a pivoting action around a pivot axis through the intersection of the arcuate resilient bands 96 and their integral flaps 94. The ribs 108 can be made even wider to provide a tighter fit between the arcuate resilient bands 96 and the cap body 98.

The cap body 98 is retained on the needle portion 82 by the engagement of the arcuate resilient bands with an annular stop bead 110 on the inner surface of the cap body 98 adjacent the large opening 106 at its proximal end. A stop bead 110 has the cross-section of a 90 degree sector of a circle with a flat surface facing toward the distal end of the cap portion 84. As an alternative, the stop bead 110 can have a semicircular cross-section, and a stop bead having a semicircular cross-section with a radius of 0.0025 inches has performed satisfactorily in a cap body 98 having an inner diameter of 0.505 inches. The cap body 98 also includes on its inner surface an annular interference bead 112 spaced from the stop bead 110 by a distance substantially greater than the axial dimension of the bands 96. The additional distance makes it easier for someone assembling the syringe assembly 80 by pushing the needle portion 82 into the cap portion 84 to stop the momentum of the needle portion 82 after the needle portion pops past the stop bead 110. This prevents the momentum of the needle portion 82 and the assembler's hand from taking the needle portion 82 past the interference bead 112 and into its extended position in which the needle 30 is exposed. After the needle portion 92 is moved past the interference bead 112, the interference bead 112 retains the cap portion 84 in an extended position enclosing the needle 30 until substantial retracting force is applied to the cap body to overcome the resilient engagement between the bands 96 and the interference bead 112.

The arcuate bands 96 have edges distal to the syringe body 14 which contact the interference bead 112 when the cap portion 84 is in its extended position. The distance between the interference bead 112 and the end of the cap body 98 having the large opening 106 is at least as great as the distance between the edges of the arcuate bands 96 which contact the interference bead when the cap portion 84 is in the extended position and an end of the needle portion 82 which is proximal to the end of the cap 98 defining the large opening 106. Therefore, when the needle portion 82 is in its retracted position and engages the interference bead 112, the rim 88 of the needle hub 86 is either flush with or is within the end of the cap body 98 defining the large opening 106. By this structure, inadvertent moving of the needle 30 into an exposed position is avoided when the needle-cap assembly 80 is carried apart from a syringe. For example, if someone puts the needle-cap assembly 80 in a pocket, extrinsic forces are likely to push the needle hub 86 and, therefore, the needle 30 forward to the point where the rim 88 of the needle hub 86 is flush with the end of the cap body 98. However, at that point, the end of the cap body substantially protects the needle hub 86 from being pushed farther forward by the extrinsic forces.

Figure 12:
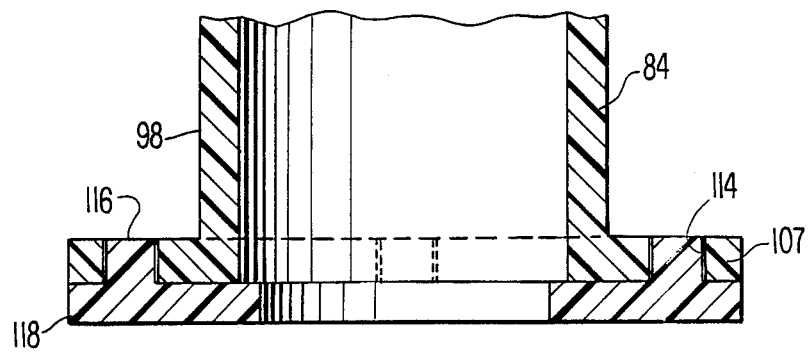
FIG. 12 is a partial cross-section of a modification of the cap portion of FIGS. 9 and 10 which employs a stop ring.

In a modification of the cap portion 84, the flange 107 can be provided with a plurality of apertures 114 for receiving posts 116 on a stop ring 118 secured to the flange 107. The stop ring has an outer diameter equal to the outer diameter of the flange 107 and an inner diameter smaller than the inner diameter of the cap body 98, and the posts 116 are held in the apertures 114 in a press fit. Thus, as can be appreciated when FIG. 12 is considered in connection with FIGS. 9 and 10, when the cap portion 98 is moved from its retracted position to its extended position, the arcuate resilient bands 96 contact the portion of the stop ring 118 extending inwardly beyond the inner surface of the cap body 98 and, thereby, prevent the cap portion 84 from separating from the needle portion 82. The stop ring 118 can be used as an alternative to the stop bead 110, or can be used in addition to the stop bead 110 for an extra margin of safety. Although FIG. 12 indicates that four evenly spaced posts 116 and a corresponding number of apertures 114 are employed, other numbers of posts and apertures can be used.

The above description is of preferred embodiments of the invention. Many modifications may be made thereto without departing from the spirit and scope of the invention, which is defined in the appended claims.

What is claimed is:

1. A no-prick assembly for a hypodermic syringe having a syringe body, comprising:
a needle portion, including a needle for injecting and withdrawing fluid, and a needle hub for mounting the needle on an end of the syringe body;
an elongate closure movably mounted on said needle portion, said closure being movable between a first position, in which said closure encloses said needle, and a second position, in which said needle projects externally of said closure, said closure having an end to be positioned proximal to said syringe body defining a large opening large enough to receive said syringe body and an end to be positioned distal to said syringe body defining a small opening large enough for said needle to pass through and small enough to prevent a human finger from passing through; and
means for supporting said closure for reciprocation relative to said needle, said supporting means comprising a plurality of radially projecting flaps and resilient portions extending from said flaps, said closure engaging said resilient portions.

2. The assembly according to claim 1, wherein said closure and said needle each define a longitudinal axis, the assembly further comprising means for maintaining the longitudinal axis of said closure in substantial alignment with the longitudinal axis of the needle.

3. The assembly of claim 1, wherein said radially projecting flaps are mounted on said needle hub.

4. The assembly of claim 1, wherein said resilient portions comprise arcuate bands, and said closure includes a generally cylindrical cap body.

5. The assembly of claim 4, wherein said flaps include portions extending radially beyond said resilient portions, and said cap body includes channels extending axially along said body, said radially extending portions of said flaps projecting into said channels, whereby said needle hub is required to rotate with said closure.

6. The assembly of claim 4, wherein the needle hub includes thread means for mounting the needle on an end of the syringe body by rotation of the needle hub in a predetermined direction relative to the syringe body.

7. The assembly of claim 6 further comprising means for locking said closure in said first position.

8. The assembly of claim 5, further comprising means for retaining said closure in said first position, wherein said retaining means comprises a widened portion in each of said channels adjacent to said proximal end to define a slot having a shoulder, said closure being twistable relative to said needle portion over a limited arc between a first orientation, in which said flaps are external to said slots, and a second orientation, in which said flaps are received in said slots and are engaged by said shoulders to prevent said closure from being moved out of said first position.

9. The assembly of claim 8, wherein the needle hub includes thread means for mounting the needle on an end of the syringe body by rotating the needle hub in a predetermined direction relative to the syringe body, and said slots are on sides of said channels opposite to said predetermined direction, whereby twisting said closure from said first orientation to said second orientation tends to tighten said thread means.

10. The assembly of claim 8, wherein said retaining means further comprises a detent to retain said closure in said second orientation.

11. The assembly of claim 10, wherein said detent comprises a resilient element positioned between said first and second orientations of said flaps.

12. The assembly of claim 1, further comprising means for retaining said closure in said first position.

13. The assembly of claim 1, further comprising means for holding said enclosure in said second position.

14. The assembly of claim 10, wherein said closure includes a flange at said proximal end of said closure, said flange defining one end of each of said channels and including slots to permit the radially extending portions of said flaps to be inserted into said closure, past said flange.

15. The assembly of claim 14, wherein the radially extending portions of said flaps have a predetermined thickness, and said flange has a side proximal to the syringe and a side distal to the syringe, said slots in said flange tapering from a first width, wider than said predetermined width, at the proximal side of said flange, to a second width, narrower than said predetermined width, at the distal side of said flange, whereby said flaps are prevented from passing back through said slots in said flange in a direction from the distal side of the flange to the proximal side of the flange.

16. The assembly of claim 14, wherein said closure further includes a retainer ring positioned adjacent to said flange, said retainer ring including ribs projecting into said slots in said flange and being held in said slots in said flange in a press fit in order to prevent said flaps from passing out through said slots in said flange and thereby to prevent said closure from separating from said syringe.

17. The assembly of claim 14, wherein bridges of material integral with said flange extend across said slots.

18. The assembly of claim 4, further comprising means for retaining said closure in said first position, wherein said arcuate bands have a first radius, and said retaining means comprises an annular bead on the interior of said cap body, said annular bead having a second radius smaller than said first radius.

19. The assembly of claim 18, wherein said needle portion has an end to be positioned proximal to the syringe body, and said arcuate bands have edges engageable with said annular bead when said closure is in said first position, the distance between said annular bead and the end of the closure having the large opening is at least as great as the distance between said edges of said arcuate bands and said proximal end of said needle portion.

20. The assembly of claim 4, further comprising means for securing said closure on said needle hub, wherein said arcuate bands have a first radius, and said securing means comprises a first annular bead on the interior of said cap body adjacent said proximal end of said closure, said first annular bead having a second radius smaller than said first radius.

21. The assembly of claim 20, wherein said arcuate bands have a dimension parallel to the longitudinal axis of said closure, and said assembly further comprises means for retaining said closure in said first position, said retaining means comprising a second annular bead having a radius smaller than said first radius, said second annular bead being spaced from said first annular bead by a distance much greater than said dimension of said arcuate bands.

22. The assembly of claim 4, further comprising means for securing said closure on said needle hub, wherein said arcuate bands have a first radius, and said securing means comprises a stop ring secured to said cap body, said stop ring having a second radius smaller than said first radius.

23. The assembly of claim 22, wherein said cap body includes an annular flange projecting radially from said proximal end, said flange defining a plurality of apertures, and said stop ring includes a plurality of posts projecting into said apertures in a press fit.

24. The assembly of claim 20, wherein said first annular bead has a surface of gradually reduced diameter facing said proximal end and a surface of sharply reduced diameter facing said distal end.

25. A no-prick hypodermic syringe assembly comprising a cylindrical syringe body having a nozzle on a distal end of said syringe body, a needle portion including a needle and a needle hub mounted on said nozzle, an elongate closure slidably engaging said needle hub, said closure having an end positioned proximal to said syringe body defining a large opening large enough to receive said cylindrical syringe body an end distal to said syringe body defining a small opening large enough for said needle to pass through and small enough to prevent a human finger from passing through, said closure being slidable on said hub between a first position in which said closure encloses said needle and a second position in which said needle projects externally of said closure thorugh said small opening and said closure telescopes over said cylindrical body, said closure and said hub having means to prevent said closure from being slid entirely off of said needle hub.

* * * * *